United States Patent [19]

Farkas et al.

[11] Patent Number: 4,554,252
[45] Date of Patent: Nov. 19, 1985

[54] PLANT TISSUE CULTIVATION PROCESS

[75] Inventors: Tibor Farkas; László Vigh; Ibolya Horváth; Anikó Nagy née Vanicsek; Ferenc Föglein, all of Szeged; Annamária Mészáros, Budapest; István Tóth, Sajóbábony, all of Hungary

[73] Assignee: Északmagyarországi Vegyimüvek, Sajóbábony, Hungary

[21] Appl. No.: 449,071

[22] Filed: Dec. 13, 1982

[30] Foreign Application Priority Data

Dec. 18, 1981 [HU] Hungary ............................. 3840/81

[51] Int. Cl.$^4$ .............................................. C12N 5/00
[52] U.S. Cl. .................................... 435/240; 435/241; 435/1; 71/118
[58] Field of Search ................... 435/240, 241; 71/118

[56] References Cited

U.S. PATENT DOCUMENTS 4,021,224  5/1977  Pallos et al. ......................... 71/118

OTHER PUBLICATIONS

Stephenson et al., Journal of Agricultural Food Chemistry, vol. 26(1) 1978, pp. 137–140.
Anonymous., Research Disclosure, vol. 143, p. 8, 1976.
Stephenson et al., Journal of Agricultural Food Chemistry, vol. 27(3), 1979, pp. 543–547.

*Primary Examiner*—Sam Rosen
*Assistant Examiner*—William J. Herald
*Attorney, Agent, or Firm*—Gabriel P. Katona

[57] ABSTRACT

Disclosed is a process for improving the efficiency of in vitro propagation and tissue cultivating by tissue culture of cultivated of plants which comprises treating the plants during micropropagation and/or subsequent planting with an aqueous solution of one or a mixture of substituted amides or one or a mixture of substituted diamides.

5 Claims, No Drawings

PLANT TISSUE CULTIVATION PROCESS

SUMMARY OF THE INVENTION

In the present invention there is provided a process for improving the growth rate of plants by tissue cultivation process.

According to the process of the present invention said improvement is achieved through treatment with a compound of the Formula (I)

wherein

R stands for methyl, chloromethyl, dichloromethyl or trichloromethyl;

$R_1$ and $R_2$ can be the same or different and stand for $C_{1-10}$ alkyl, $C_{2-10}$ alkenyl, 3–9 cycloalkyl, phenyl or benzyl; or hydrogen with the proviso that at least one of the symbol(s) $R_1$ and $R_2$ is (are) other than hydrogen; or $R_1$ and $R_2$ form together with the nitrogen atom to which they are attached a 5 to 8 membered saturated heterocyclic ring which may contain one, two or three identical or different further heteroatom(s), preferably oxygen or nitrogen atom(s); or with a compound of the Formula (II)

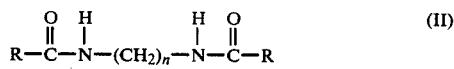

wherein

R is as defined at formula (I) and
n is an integer between 1 and 8.

BACKGROUND AND PRIOR ART

In vitro tissue cultivating plant propagation methods have become widespread in the last two decades. In the United States more than twenty and in West-Europa numerous propagating laboratories are operating in which between one hundred thousand and two hundred thousand plants are produced per month by means of the tissue cultivating process.

From the practical point of view the main features of tissue cultivating propagation are as follows: from the meristematic tissues of the sprout tips and root tips under sterile conditions, plants, free from all kinds of plants pathogens, can be propagated with a velocity which is several orders of magnitude higher than that of the conventional propagation method, with a significantly smaller area demand and consequently in a much more economical way than according to the conventional propagating methods.

In Hungary the large scale use of the tissue cultivating plant propagation method is under progress.

Although the tissue cultivating propagation is more economical than the conventional propagation methods, its inherent advantages can not be utilized owing to various drawbacks.

The major disadvantage of the tissue cultivating propagation method resides in the fact that while under in vitro conditions on unrestricted propagation of the plants takes place, when planted into the soil—depending on the type of the plant culture—about from 20 to 60% of the plants grown under sterile conditions are destroyed under the new, less favourable in vivo conditions [Broome, Zimermann: Hort. Science. 13, 151–153 (1978); Earle, Langhans: Hort. Science, 10, 608–610 (1975); Sutter, Langhans: J. Am. Soc. Hort. Science, 104, 494–496 (1979)].

Although several efforts were made to enhance the efficiency of propagation by improving the technical conditions of in vivo culturing (smaller temperature fluctuation, relatively high humidity), said measures failed to give the desired result.

DETAILED DESCRIPTION OF THE INVENTION

The aim of our investigations directed to the tissue cultivating propagation process is to detect the cause of the poor adaptability of the plants taken out from the flask and that of the small survival rate of the plants.

The object of the present invention is to provide a process which significantly improves the efficiency of the tissue cultivating method and ensures that a large majority of the in vitro propagated plants remain viable and strongly develop under in vivo conditions too.

In glass house and field experiments we have studied the composition of waxes and membrane lipids and also the biosynthesis of the cell components of various cultivated plants (carnation, gerbera, grape, fern). As a summary of said experiments significant modifications and changes have been found in the structure of the above-mentioned cell components of plants propagated by tissue cultivation.

It has been found that the synthesis of the waxes coating the surface of the leaves of the plants grown in flasks is inhibited. It has also been found that while in the lipophyl component of the cell membrane of plants cultivated by conventional methods highly unsaturated fatty acids are synthesised, in the case of plants propagated by tissue cultivation the synthesis of highly unsaturated fatty acids is inhibited. As a consequence thereof the cell membranes become brittle and can not perform the various membrane functions.

According to a series of experiments the composition of the wax components of plants propagated by the conventional method and the in vitro propagation process, respectively, has been determined by an isotope technique. The plants are incubated in a labelled 1-$^{14}$C acetate solution having an activity of 10 $\mu Ci/\mu mole$ at 25° C. for 4 hours, whereupon the waxy components are separated by means of thin layer chromatography and their ratio is determined on the basis of the specific activity.

The results of the above series of experiments are summarized in the following Table:

| | Percental distribution of the waxy components | | | | | | |
|---|---|---|---|---|---|---|---|
| | Acid | Hydroxy diketone | Primary alcohol | Secondary alcohol | Aldehyde | Ester | Hydrocarbon |
| Control | 31.13 | 3.32 | 19.44 | 1.53 | 14.33 | 5.40 | 24.84 |
| In vitro | 42.56 | in traces | 3.24 | 2.04 | 20.95 | 2.71 | 28.48 |

The above comparative data show that in the waxes of in vitro propagated plants the distribution of the components differs considerably from that of the control plants. The accumulation of the acids increases the permeability of the surface of the leaves and the smaller amount of primary alcohols exhibits a similar effect.

The above two courses of procedure take place simultaneously and have the result that the in vitro propagated plants are incapable of maintaining the water content of the cells when set out in the field (in vivo).

In a further experiment the fatty acid composition of total lipids isolated from plants propagated by the conventional method and also from the in vitro propagated plants has been determined. The results are disclosed in the following Table:

| Name | Percental fatty acid composition of the lipids | | | | | |
|---|---|---|---|---|---|---|
| | palmitic acid | palmitoleyl acid | stearic acid | oleic acid | linolic acid | linolenic acid |
| Carbon atom number | 16 | 16 | 18 | 18 | 18 | 18 |
| Number of unsaturated bonds | 0 | 1 | 0 | 1 | 2 | 3 |
| Control | 14.72 | 0.79 | 0.59 | 5.53 | 30.29 | 48.07 |
| In vitro | 25.82 | 3.52 | 7.11 | 27.97 | 17.18 | 18.04 |

A comparison of the fatty acid composition shows that in the lipids of the in vitro propagated plants oleic acid is accumulated. It can be presumed that the desaturation of oleic acid into linolenic acid is inhibited for certain reasons. Fatty acids containing more than one unsaturated bond (e.g. acid and linolenic acid) play an important role in the flexibility of the cell membranes and thus in the adaptability of the plants. If the cell membranes contain no unsaturated fatty acids, the adaptability of the plants is decreased to a significant extent.

The above data show that in the in vitro propagated plants the biosynthesis of waxes coating the surface of the leaves and particularly that of fatty acids appearing in the cell membrane sustains damages and consequently the seedlings planted from the flask into the soil are no more capable of standing even a small temperature fluctuation, and due to the lesions of the membrane the plants become dry even under relatively high humidity, and a significant percentage of the plants is killed.

In view of the above knowledge, our experiments have been directed to influence the composition of the waxy components, the ratio of the fatty acids of lipids and their biosynthesis during the in vitro propagation.

An object of our invention is to provide a process which is capable of significant decrease of the postplantation damages of in vitro cultivated plants and also of improvement of the adaptability of the plants.

It has been found that when in the course of the known tissue cultivating propagation process the tissues are treated with an aqueous solution of a compound of the formula I or II (wherein R, $R_1$, $R^2$ and n have the same meaning as stated above) or a mixture thereof; significantly less in vitro cultivated plants are killed after planting under in vivo conditions; significantly more plants survive the planting and the development of the surviving plants also get stronger.

The compounds of the Formula (I) and (II) are known, resp., can be prepared according to the following literature sources: [Res. Discl. (1976) 143-8; J. Agric. Food. Chem., 26, (1) 137-140 (1978) and J. Agric. Food. Chem., 27, (3), 543-547 (1979)].

The plants can be treated with the compounds of the formula (I) or (II) by the following methods:

The compound of the formula I or II or a mixture of compounds of formula I or a mixture of compounds of formula II is dissolved in the nutrient medium to be applied onto the roots to give a concentration of 1-100 mg./l., preferably of 1-20 mg./l. One may also proceed by dipping the seedlings grown in a root-forming nutrient medium into an aqueous solution of a compound of the general formula I or II having a concentration of 1-20 mg./l. 20-70 mg./l., prior to planting (i.e. the rootsystem of the plants is dipped into the solution). The treatment can also be carried out by planting the in vitro cultivated seedlings into a soil mixture soaked with an aqueous solution of 2-10 mg./l. of a compound of the formula I or II. According to an other embodiment of the process of the present invention the in vitro cultivated and planted seedlings are sprayed with an aqueous solution of a compound of the formula I or II having a concentration of 1-20 mg./l., preferably of 5-12 mg./l. and said spraying treatment is repeated several times if necessary.

Further tests have been carried out to determine the changes of the main waxy components in the plants propagated by the tissue cultivating method and subjected to treatment with an aqueous solution of a compound of formula I or II as compared to the untreated plants. The effect of the treatment on the fatty acid composition of the total lipids of the plants have also been examined.

In the course of the above test a nutrient medium having the following composition is used in the in vitro cultivating of the plants:

| [Murashige, T., Skoog, F.: Physiol. Plant. 15, 473-497 (1962)] | | | |
|---|---|---|---|
| $CaCl_2 \times 2H_2O$ | 439.300 mg./l | $Zn_2SO_4 \times 7H_2O$ | 8.600 mg./l. |
| $CoCl_2 \times 2H_2O$ | 0.025 mg./l. | sugar | 3-45.000 g./l. |
| $CuSO_4 \times 5H_2O$ | 0.025 mg./l. | inositol | 100.000 mg./l. |
| FeNa EDTA | 336.600 mg./l. | nicotic acid | 10.000 mg./l. |
| $H_3BO_3$ | 6.200 mg./l. | thiamine hydrochloride | 30.000 mg./l. |
| $KH_2PO_4$ | 170.000 mg./l. | pyridoxine hydrochloride | 10.000 mg./l. |
| KJ | 0.830 mg./l. | adenine sulfate $\times 2H_2O$ | 0-80.000 mg./l. |
| $KNO_3$ | 1.900.000 mg./l. | indolyl acetic acid | 0-10.000 mg./l. |
| $MgSO_4 \times 7H_2O$ | 370.600 mg./l. | quinetine | 0-30.000 mg./l. |
| $MnSO_4 \times 4H_2O$ | 22.300 mg./l. | agar—agar | 7-10.000 g./l. |
| $NaH_2PO_4 \times 2H_2O$ | 96.000 mg./l. | | |
| $Na_2MoO_4 \times 2H_2O$ | 0.250 mg./l. | | |
| $NH_4NO_3$ | 1.650.000 mg./l. | | |

The above components are dissolved in distilled water, the pH of the solution is adjusted to 5.8, agar—agar is added, the nutrient medium is warmed until it becomes clear whereupon it is filled under sterile conditions into flasks, the mouth thereof having been closed with paper stoppers. The flasks are placed into an autoclave and sterilized at a temperature of 121° C.

In the first series of tests the effect of dichloro acetyl hexamethylene imine (a compound of the formula I) on the synthesis of the main waxy components of carnation is determined. Plants are cultivated by the conventional method on the one hand and the in vitro tissue cultivating method on the other hand on nutrient media having the above composition and on those to which 6 mg./l. of dichloro acetyl hexamethylene imine were added prior to the sterilization of the nutrient media. In identical growth stage of the plants the percental amount of the two most important waxy components is determined by the method disclosed above. The results obtained are summarized in the following Table:

| Cultivating method | Fatty components, % | |
|---|---|---|
| | Acids | Primary alcohols |
| Conventional (control) | 32.11 | 20.55 |
| In vitro | 45.21 | 3.05 |
| Process of the present invention in vitro | 30.73 | 22.18 |

The above experimental data clearly show that as a result of the dichloro acetyl hexamethylene imine treatment the composition of the waxy components of in vitro cultivated carnation plants returns to the level determined in plants cultivated by the conventional methods.

In the following series of tests the effect of various concentrations of dichloro acetyl hexamethylene imine on the fatty acid composition of total lipids of in vitro cultivated carnation plants is determined. Carnation seedlings are in vitro cultivated in nutrient media having the composition disclosed above (250 ml. each) and containing various amounts of dichloro acetyl hexamethylene imine. The fatty acid composition of the total lipids is determined in the same growth stage of the plants by the methods disclosed above.

The results are summarized in the following Table:

| Concentration by treatment [mg./l.] | Fatty acid, % | | | | | |
|---|---|---|---|---|---|---|
| | Palmitic acid | Palmitoleyl acid | Stearic acid | Oleic acid | Linolic acid | Linolenic acid |
| 0.00 | 25.82 | 3.89 | 7.11 | 27.97 | 17.18 | 18.04 |
| 15.60 | 25.16 | — | 3.09 | 18.94 | 32.85 | 23.96 |
| 30.80 | 23.08 | — | 4.37 | 18.53 | 25.18 | 28.85 |
| 61.60 | 24.61 | — | 2.50 | 16.68 | 32.85 | 23.26 |
| 154.00 | 21.13 | — | 3.38 | 19.15 | 29.20 | 27.04 |
| 308.00 | 26.57 | — | 4.00 | 25.71 | 25.29 | 18.43 |

It clearly appears from the above data that the treatment carried out with different concentrations of dichloro acetyl hexamethylene imine shifted the fatty acid composition towards the unsaturated fatty acids.

EXAMPLES

Further details of the present invention are to be found in the following Examples without limiting the scope of protection to the same Examples.

EXAMPLE 1

Preparation of propagative material of carnation by tissue cultivation

Meristemical tissues of carnation cuttings cultivated by conventional methods in glass-house are isolated under sterile conditions and propagated in the Murashige-Skoog nutrient medium disclosed above. At first the carnation meristema had started growing and later multiplied by bipartition. From each sprout tip 10-15 shoots developed within six weeks from being placed on the nutrient medium. After having been taken apart the said shoots are suitable for further propagation in a new fresh nutrient medium. The propagation velocity in the shoots amounts to 10-15 shoots pro month.

The multiplying phase of the carnation shoots having been completed the induction of root-formation takes place in a separate nutrient medium for which purpose a five-fold dilution of the basic nutrient medium is used, to which 0.1 mg./l. of indolyl acetic acid is added.

From the nutrient medium a concentration series is prepared by adding various amounts of dichloro acetyl hexamethylene imine; cultivation is carried out on the nutrient media thus obtained.

When the root formation has reached the desired extent, the carnation seedling are placed into glass house and cultivated under in vivo conditions.

The planted seedlings adapted themselves to the conditions of in vivo cultivation to a different extent. Some of them showed a good adaption, survived plantation and developed well.

In the course of in vivo propagation the killed and survived plants cultivated on different nutrient media are counted and the percentage is disclosed in the following Table:

| Dichloro acetyl hexamethylene imine content of the nutrient medium [mg./l.] | Survival, % |
|---|---|
| 1 | 45 |
| 2 | 48 |
| 4 | 64 |
| 6 | 96 |
| 8 | 87 |
| 10 | 75 |
| 12 | 70 |
| 14 | 50 |
| 20 | 43 |
| 0 (control) | 46 |

The above data show that on adding 6 mg./l. of dichloro acetyl hexamethylene imine to the nutrient medium the glass house survival rate of carnation seedlings can be increased to 96%, i.e. the efficiency of the propagating method can be increased by more than 100% (i.e. to the double) which significantly improves the economy of the process.

It can be observed that the seedlings cultivated by the process of the present invention show a deeper green tonality, their stems and leaves are stronger than those of the control seedlings and the surface of the leaves is coated by a thicker waxy layer.

EXAMPLE 2

Carnation propagation material is prepared in an analogous manner to the preceding Example. The meristema tissues are propagated on the Murashiga-Skoog nutrient medium referred to above. In order to induce root-formation the plants are planted into a five-fold diluted nutrient medium containing 0.1 mg./l. of indolyl acetic acid. The in vitro cultivated seedlings are planted in a glasshouse into a soil mixture soaked with a solution of dichloro acetyl hexamethylene imine as follows: 5 g. of dichloro acetyl hexamethylene imine are dissolved in 500 ml. of 70% ethanol and the solution is admixed with 20 l. of water. The solution thus obtained (20 l.) is added to 1 m³ of soil mixture which has been turned through several times. The in vitro cultivated plants are planted on the one hand into the soil thus treated and on the other into untreated soil and the in vivo growth is observed in glass house.

It has been found that while in untreated soil 58% of the seedlings are killed (i.e. only 42% survived the plantation), in the soil treated with dichloro acetyl methylene imine only 8% of the seedlings are destroyed (i.e. the survival rate amounts to 92% and these plants developed vigorously).

EXAMPLE 3

Carnation propagating material is produced in an analogous manner to Example 2 and after the root system has been developed the seedlings are planted into untreated soil in a glass house for in vivo cultivation.

Half of the planted seedlings are treated with a spray containing dichloro acetyl hexamethylene imine after plantation and three further times with intervals of 3–4 days.

The spray contains 10 mg. of dichloro acetyl hexamethylene imine, 0.1 ml. of Tween 80 emulsifier and 0.05 molar TRIS HCl buffer per liter; the pH amounts to 6.5. The spray is prepared by dissolving the dichloro acetyl hexamethylene imine in a few drops of 70% ethanol, adding the solution to the mixture of water and the buffer and thereafter adding the emulsifier.

It has been found that while 88% of the treated seedlings survive the plantation, in the untreated group the survival rate amounts but to 42%.

EXAMPLE 4

Production of gerbera propagating material by tissue cultivation

Gerbera plants are in vitro propagated by the known propagating and rooting method of Murashagi et al. [J. Hort. Sci. 9, 175–180 (1974)]. To a part of the root-forming nutrient medium dichloro acetyl hexamethylene imine is added in a concentration of 10 mg./l. and half of the seedlings are cultivated in this nutrient medium.

The in vitro cultivated seedlings are planted in a glass house and further cultivated under in vivo conditions. The killed and surviving seedlings are counted.

It has been found that on plants root-drenched with a nutrient medium containing 10 mg./l. of dichloro acetyl hexamethylene imine the survival rate amounts to 98–100% while that of the untreated control plants is only 65–70%.

The habitus of the gerbera plant cultivated in flask has significantly changed, because the plants got stubbier, their leaves harder and stronger developed in the case of the treated plants.

EXAMPLE 5

Carnation propagating material is produced by tissue cultivating in an analogous manner to Example 1 except that in order to induce root-formation to the five-fold diluted basic nutrient medium in the place of 0.1 mg./l. indolyl acetic acid 0.1 mg./l. of p-chloro-phenoxy acetic acid are added.

Thereafter various concentrations of compounds of the formula I or II (2; 5; 10 and 20 mg./l.) are added to the nutrient medium and the plants are cultivated on the nutrient media until the root system has developed.

Once the root system has reached a size suitable for plantation, the seedlings are set out in glass house and cultivated.

The seedlings adapted themselves to the in vivo conditions in a different manner.

After a uniform and safe development the number of the killed and surviving seedlings is counted and their ratio is determined.

The results are summarized in the following Table:

| Compound of the formula I or II | Percental ratio of the rooted and surviving seedlings in the concentration of the compound of the formula I or II amounts to | | | |
|---|---|---|---|---|
| | 2 mg./l. | 5 mg./l. | 10 mg./l. | 20 mg./l. |
| Untreated control | 61 | 61 | 61 | 61 |
| N—acetyl-hexamethylene-imine | 80 | 81 | 80 | 81 |
| N—(chloro-acetyl)-hexamethylene imine | 76 | 76 | 76 | 70 |
| N—(dichloro-acetyl)-hexamethylene imine | 100 | 100 | 100 | 100 |
| N—(trichloro-acetyl)-hexamethylene imine | 65 | 65 | 63 | 63 |
| N—dichloroacetyl) diisobutyl-amine | 68 | 66 | 77 | 61 |
| N—(dichloro-acetyl)-isopropyl-amine | 72 | 71 | 71 | 71 |
| N—(dichloro-acetyl)-tert.butyl-amine | 71 | 72 | 72 | 72 |
| N,N'—bis-(dichloro-acetyl)-hexamethylene diamine | 95 | 100 | 100 | 95 |
| N—(dichloroacetyl)-hexyl amine | 94 | 95 | 98 | 100 |

The above data proved on the one hand that as a result of replacing indolyl acetic acid by p-chloro-phenoxy acetic acid the survival rate of carnation seedlings is increased from 46% to 61%, while on the other hand that the use of the compounds of the formula I or II further improve the post-plantation viability.

It has also been found that the stems and leaves of the carnation seedlings cultivated by the process of the present invention are stronger and of a deeper green colour than those of the untreated control plants.

EXAMPLE 6

Gerbera propagating material is produced by tissue cultivation according to Example 5. The chemical name of the compound of the formula I or II used, the concentration applied and the survival rate are summarized in the following Table.

| Compound of the formula I or II | Percental ratio of the rooted and surviving seedlings in the concentration of the compound of the formula I or II amounts to | | | |
|---|---|---|---|---|
| | 2 mg./l. | 5 mg./l. | 10 mg./l. | 20 mg./l. |
| Untreated control | 63 | 63 | 63 | 63 |
| N—acetyl-hexamethylene-imine | 83 | 84 | 83 | 82 |
| N—(chloro-acetyl)-hexamethylene imine | 78 | 82 | 79 | 80 |
| N—(dichloro-acetyl)-hexamethylene imine | 100 | 100 | 100 | 100 |

-continued

| Compound of the formula I or II | Percental ratio of the rooted and surviving seedlings in the concentration of the compound of the formula I or II amounts to | | | |
|---|---|---|---|---|
| | 2 mg./l. | 5 mg./l. | 10 mg./l. | 20 mg./l. |
| N—(trichloro-acetyl)-hexamethylene imine | 70 | 69 | 68 | 68 |
| N—(dichloroacetyl) diisobutyl-amine | 73 | 72 | 70 | 70 |
| N—(dichloro-acetyl)-isopropyl-amine | 75 | 73 | 74 | 73 |
| N—(dichloro-acetyl)-tert.butyl-amine | 75 | 75 | 75 | 72 |
| N,N'—bis-(dichloro-acetyl)-hexamethylenediamine | 100 | 100 | 100 | 100 |
| N—(dichloroacetyl)-hexyl amine | 100 | 100 | 100 | 100 |

EXAMPLE 7

The process described in Example 5 is used on thorn-free blackberry. The results are set forth in the following Table.

| Compound of the formula I or II | Percental ratio of the rooted and surviving seedlings in the concentration of the compound of the formula I or II amounts to | | | |
|---|---|---|---|---|
| | 2 mg./l. | 5 mg./l. | 10 mg./l. | 20 mg./l. |
| Untreated control | 65 | 65 | 65 | 65 |
| N—acetyl-hexa-methylene-imine | 85 | 86 | 86 | 86 |
| N—chloro-acetyl)-hexamethylene imine | 80 | 82 | 81 | 80 |
| N—(dichloro-acetyl)-hexamethylene imine | 100 | 100 | 100 | 100 |
| N—(trichloro-acetyl)-hexamethylene imine | 70 | 70 | 70 | 70 |
| N—(dichloroacetyl) diisobutyl-amine | 70 | 68 | 65 | 65 |
| N—(dichloro-acetyl)-isopropyl-amine | 75 | 76 | 75 | 74 |
| N—(dichloro-acetyl)-tert.butyl-amine | 75 | 75 | 75 | 72 |
| N,N'—bis-(dichloro-acetyl)-hexamethylenediamine | 100 | 100 | 100 | 100 |
| N—(dichloro-acetyl)-hexyl amine | 100 | 100 | 100 | 100 |

EXAMPLE 8

Grape propagating material is produced by the tissue cultivating method according to the method of Example 5. The chemical name of the compound of the formula I or II, the concentration applied and the survival rate are disclosed in the following Table.

| Compound of the formula I or II | Percental ratio of the rooted and surviving seedlings in the concentration of the compound of the formula I or II amounts to | | | |
|---|---|---|---|---|
| | 2 mg./l. | 5 mg./l. | 10 mg./l. | 20 mg./l. |
| Untreated control | 62 | 62 | 62 | 62 |
| N—acetyl-hexa-methylene-imine | 81 | 84 | 84 | 85 |
| N—(chloro-acetyl)-hexamethylene-imine | 73 | 72 | 70 | 68 |
| N—(dichloro-acetyl)-hexamethylene imine | 100 | 100 | 100 | 100 |
| N—(trichloro-acetyl)-hexamethylene imine | 65 | 65 | 63 | 63 |

-continued

| Compound of the formula I or II | Percental ratio of the rooted and surviving seedlings in the concentration of the compound of the formula I or II amounts to | | | |
|---|---|---|---|---|
| | 2 mg./l. | 5 mg./l. | 10 mg./l. | 20 mg./l. |
| N—(dichloroacetyl) diisobutyl-amine | 72 | 70 | 68 | 66 |
| N—(dichloro-acetyl)-isopropyl-amine | 72 | 72 | 71 | 69 |
| N—(dichloro-acetyl)-tert.butyl-amine | 72 | 72 | 70 | 70 |
| N,N'—bis-(dichloro-acetyl)-hexamethylenediamine | 100 | 100 | 100 | 100 |
| N—(dichloro-acetyl)-hexyl amine | 100 | 100 | 100 | 100 |

EXAMPLE 9

The process according to Example 5 is used for the propagation of apple stock made virus free. The chemical name of the compounds of the formula I or II, the concentration used and the survival rate are set forth in the following Table.

| Compound of the formula I or II | Percental ratio of the rooted and surviving seedlings in the concentration of the compound of the formula I or II amounts to | | | |
|---|---|---|---|---|
| | 2 mg./l. | 5 mg./l. | 10 mg./l. | 20 mg./l. |
| Untreated control | 70 | 70 | 70 | 70 |
| N—acetyl-hexa-methylene-imine | 83 | 85 | 85 | 85 |
| N—(chloro acetyl)-hexamethylene-imine | 83 | 79 | 79 | 75 |
| N—(dichloro-acetyl)-hexamethylene-imine | 100 | 100 | 100 | 100 |
| N—(trichloro-acetyl)-hexamethylene imine | 74 | 78 | 78 | 72 |
| N—(dichloroacetyl) diisobutyl-amine | 80 | 82 | 80 | 80 |
| N—(dichloro-acetyl)-isopropyl-amine | 80 | 81 | 80 | 79 |
| N—(dichloro-acetyl)-tert.butyl-amine | 90 | 91 | 90 | 89 |
| N,N'—bis-(dichloro-acetyl)-hexamethylenediamine | 100 | 100 | 100 | 100 |
| N—(dichloro-acetyl)-hexyl amine | 100 | 100 | 100 | 100 |

The process of the present invention can be effectively used for the improvement of the efficiency of tissue cultivating propagation of cultivated and ornamental plants and also for the increase of the past-plantation survival rate of the seedlings. A further advantage of the process of the present invention resides in the fact that the stems and leaves of the thus propagated plants are stronger and more developed, their colour is of a darker tonality and the wax layer on the leaves is thicker than that of the plants propagated by conventional methods.

A further advantage of the process of the present invention is that the seedlings treated with a solution of a compound of the formula I or II begin to grow more rapidly and reach the desired size earlier than those propagated by the conventional methods.

We claim:

1. A process for improving the efficiency of in vitro propagation and tissue cultivation by tissue culture of cultivated plants, which comprises the step of:

treating the seeds or the roots of seedlings during micropropagation and subsequent planting or during micropropagation or subsequent planting, with an aqueous solution of 1–100 milligrams per liter of a compound of the formula

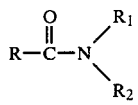

or mixtures thereof, or a compound of the formula

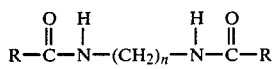

or mixtures thereof; wherein

R is methyl, chloromethyl, dichloromethyl or trichloromethyl;

$R_1$ and $R_2$ are each independently hydrogen, alkyl containing between 1 and 10 carbon atoms, alkenyl containing between 2 and 10 carbon atoms, cycloalkyl containing between 3 and 9 carbon atoms, phenyl, or benzyl, with the proviso that at least one of $R_1$ and $R_2$ is other than hydrogen; and n is an integer from 1 to 8.

2. The process of claim 1, for propagation on liquid nutrient medium, which comprises using a liquid nutrient medium containing 1–20 milligrams per liter of a compound or a mixture of compounds of formula I or a compound or a mixture of compounds of formula II.

3. The process of claim 1, which comprises prior to planting, soaking the root system of plants propagated on liquid nutrient medium in a solution of 20–70 milligrams per liter of a compound or a mixture of compounds of formula I or a compound or a mixture of compounds of formula II.

4. The process of claim 1, which comprises planting the in vitro propagated seedlings in a soil mixture soaked with an aqueous solution of 2–10 milligrams per liter of a compound or a mixture of compounds of formula I or a compound or a mixture of compounds of formula II.

5. The process of claim 1, which comprises planting the in vitro propagated seedlings and then spraying them with a solution of 1–20 milligrams per liter of a compound or a mixture of compounds of formula I or a compound or a mixture of compounds of formula II.

* * * * *